(12) United States Patent
Plachta et al.

(10) Patent No.: US 11,712,558 B2
(45) Date of Patent: Aug. 1, 2023

(54) MEDICAL IMPLANT OF THE TYPE OF A WRAP-AROUND CUFF ELECTRODE ASSEMBLY

(71) Applicant: Neuroloop GmbH, Freiburg (DE)

(72) Inventors: Dennis Plachta, Freiburg (DE); Fabian Kimmig, Freiburg (DE); Tim Boretius, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 0 days.

(21) Appl. No.: 17/266,363

(22) PCT Filed: Aug. 5, 2019

(86) PCT No.: PCT/EP2019/071025
§ 371 (c)(1),
(2) Date: Feb. 5, 2021

(87) PCT Pub. No.: WO2020/030592
PCT Pub. Date: Feb. 13, 2020

(65) Prior Publication Data
US 2021/0316138 A1    Oct. 14, 2021

(30) Foreign Application Priority Data
Aug. 6, 2018  (DE) .................... 10 2018 213 120.1

(51) Int. Cl.
*A61N 1/05* (2006.01)
*A61N 1/36* (2006.01)

(52) U.S. Cl.
CPC ......... *A61N 1/0556* (2013.01); *A61N 1/3605* (2013.01)

(58) Field of Classification Search
CPC .. A61N 1/0556; A61N 1/3605; A61N 1/0582; A61N 2001/0582
See application file for complete search history.

(56) References Cited

U.S. PATENT DOCUMENTS

| | | | | |
|---|---|---|---|---|
| 5,938,596 | A | * | 8/1999 | Woloszko ............ A61N 1/0556 600/377 |
| 2011/0147046 | A1 | * | 6/2011 | Bonde .................. A61N 1/0556 174/126.1 |

(Continued)

FOREIGN PATENT DOCUMENTS

| CA | 2139097 A1 | 6/1996 |
|---|---|---|
| DE | 10 2016 222 712 A1 | 5/2018 |

(Continued)

OTHER PUBLICATIONS

International Search Report for PCT/EP2019/071025, dated Nov. 25, 2019; English translation submitted herewith (6 pgs.).

*Primary Examiner* — Alyssa M Alter
(74) *Attorney, Agent, or Firm* — Fitch, Even, Tabin & Flannery LLP

(57) ABSTRACT

The invention is a medical implant which is a wrap-around cuff comprising a flexible, biocompatible, film carrier substrate, that has a carrier substrate region which is wrapped around a wrap axis to form a tube. The invention has a protective structure directly or indirectly attached to the carrier substrate, which can be transformed from a first, open state into a second closed state that encloses the carrier substrate region that is wrapped to form a tube at least axially around a wrapping axis extending in the peripheral direction of the tube.

13 Claims, 6 Drawing Sheets

(56) References Cited

U.S. PATENT DOCUMENTS

| | | |
|---|---|---|
| 2012/0192874 A1 | 8/2012 | Bolea et al. |
| 2012/0277819 A1 | 11/2012 | Cowley et al. |
| 2013/0123895 A1 | 5/2013 | Bonde et al. |
| 2019/0320921 A1 | 10/2019 | Kimmig et al. |

FOREIGN PATENT DOCUMENTS

| | | |
|---|---|---|
| WO | 2013/159136 A1 | 10/2013 |
| WO | 2016/055512 A1 | 4/2016 |

* cited by examiner

MEDICAL IMPLANT OF THE TYPE OF A WRAP-AROUND CUFF ELECTRODE ASSEMBLY

CROSS-REFERENCE TO RELATED APPLICATIONS

Reference is made to International Application No. PCT/EP2019/071025, filed Aug. 5, 2019, which claims priority to German Patent Application No. 10 2018 213 120.1, filed Aug. 6, 2018, the contents of which are incorporated herein by reference in their entirety.

FIELD OF THE INVENTION

The invention relates to a medical implantable wrap-around cuff electrode assembly, cuff electrode in short, which comprises a biocompatible, film carrier substrate, that has the first carrier substrate region, which upon wrapping around a wrapping axis, forms a tube.

DESCRIPTION OF THE PRIOR ART

Electronic implants which are suitable for permanent or at least long-term placement in the body, are typically used for the therapeutic influencing of organ functions. Among the wide variety of implants differently designed and specially assembled implants for different therapeutic applications. Further considerations mainly relate to an implant designed as a wrap-around electrode assembly, also known as a cuff electrode, that is specially configured for intracorporeal application and for as permanent as possible fastening along a nerve fiber bundle in order at least to apply electrical stimulation signals to the nerve fiber bundle as required.

A medical implant of this type, suitably configured in the manner of a wrap-around cuff for the purpose of detection as well as application of neuronal electrical signals for permanent or at least long-term positioning along a nerve fiber bundle within the human or animal body is described in document WO 2016/055512 A1 and is also shown schematically in FIG. 2. The medical implant 1 made of a biocompatible, flat or film-like surface substrate 2 and configured as a wrap-around cuff, comprises a first carrier substrate region 3 which is wrapped around a spatial axis 5 to form at least one substrate wrapping, preferably forming one and a half, two or multiple substrate wrappings which are radially surrounded in a straight cylindrical hollow space H. Attached on the substrate surface facing the straight cylindrical hollow space H are electrode surfaces, not shown in FIG. 2, which come into direct or indirect physical contact with the epineurium of a nerve fiber bundle, also not shown in FIG. 2, which are surrounded by the wrap-around cuff 1. In order to guarantee that on the one hand the medical implant 1 remains as fixed in place as possible along a nerve fiber bundle after corresponding implantation, and on the other hand can follow the natural changes in shape of the nerve fiber bundle or at least does not subject this to any significant mechanical resistance, the individual substrate wrappings adjoin each other loosely and can, in the event of expansion of the nerve fiber bundle, increase the diameter of the encompassed hollow space H through appropriate relative movement.

Through material pre-tensioning introduced into the substrate carrier 2 in a first carrier substrate region 3, the surface carrier 2 takes on a predefined wrapping configuration without the effect of external forces. The free section end 4 is at least loosely covered by at least one layer of the first carrier substrate region 3, that is radially covered by at least one wrap of the surface substrate wrapping.

In this form of embodiment, adjoining the wrapped first carrier substrate region 3 in one piece is a second carrier substrate region 6, which is not wrapped around the spatial axis 5, within which electrical supply and discharge leads are guided that are connected to the electrodes which directly or indirectly come into contact with the epineurium of the nerve fiber bundle. In this embodiment as shown, the also flat second carrier substrate region 6 comprises a web-like surface region 61 orientated in parallel to the spatial axis 5, which via an interface S, (which is not shown in more detail) in the form of an implantable plug connection S, for example, connected to a connection structure 7 leading away from the medical implant 1, along which the electrical leads extend to a separate, preferably implantable, supply unit in the form of a control device or an energy source.

In an unstressed state, the mechanical implant 1 lies along a nerve fiber bundle N in accordance with the schematic view in FIG. 3a uniformly encloses the diameter of the first substrate region 3 shaped into a wrap-around cuff. In this state, no force, or only a minimal mechanical external force acts on the nerve fiber bundle N. On the other hand, if external forces F, originating, for example, from the body's own movements, acts on the medical implant 1, deformations of the wrapping geometry can occur along the first substrate portion 3 configured as a wrap-around cuff, through which the fastening of the medical implant along the nerve fiber bundle N can no longer be guaranteed, and on the other hand, a mechanical stress can act on the nerve fiber bundle through the medical implant. Such tensile stress situations F are in FIGS. 3b to e. Thus, for example, tensile forces F, which are essentially orientated in parallel to the longitudinal extension of the nerve fiber bundle N result in a funnel-shaped deformation within the wrap-around cuff which on the one hand leads to a constriction E on the nerve fiber bundle N, and on the other hand to a widening A, and associated radial distancing of the wrap-around cuff from the nerve fiber bundle N as shown in FIGS. 3b and c. Constriction E of the nerve fiber bundle N can also occur in the case of a force F, orientated orthogonally to the longitudinal extension of the nerve fiber bundle, acting on the medical implant 1, as shown as the stress situation illustrated in FIG. 3d. In this case the force F acts as a tensile force acts transversely to the nerve fiber bundle N. In FIG. 3e, the force acts in the opposite force direction as a thrust force F directed onto the nerve fiber bundle N, through which the wrap-around cuff widens in diameter and tends to become detached from the nerve fiber bundle N.

Cuff electrodes of the type in question when implanted for the long term, are also subject to a further disadvantageous effects which can lead to functional impairments and to making possibly required surgical removal of the cuff electrode from the nerve fiber more difficult and which is caused by natural tissue growth, through which the cuff electrode well and truly becomes grown in along the nerve fiber bundle or is completely overgrown by tissue. Because of the loose carrier substrate wrapping within the first carrier substrate region wrapped to form a tube, growth-related areas of tissue could also penetrate between individual substrate layers.

Another type of cuff electrode is described in US published patent application 2013/0123895 A1, which in contrast to a wrap-around electrode, comprises a cuboid basic body onto which two lobe-shaped flat sections are applied which, overlap each other in one layer and surround a nerve.

Through the mutual surrounding of both flat sections, the radially outer lying flat section stabilises the radially inner lying flat section.

SUMMARY OF THE INVENTION

The invention is a further development of a medical implant of a wrap-around cuff electrode assembly, cuff electrode in short, which comprises a biocompatible, film carrier substrate, that comprises a carrier substrate region, which through being wrapped around a wrapping axis, assumes the form of a tube, in such a way that the aforementioned drawbacks with regard to tensile force caused, mechanical stresses and the wrap-around cuff deformations resulting therefrom, as well as the tissue growth-associated overgrowing of the cuff electrode and the connected risks of injury in the case of required surgical removal of the implant from the nerve fiber bundle, are significantly reduced or completely avoided. In addition, the invention secures the implant against dislocation and complete detachment from the intracorporeal vessel or nerve fiber bundle.

According to the invention, a medical implant in the form of a cuff electrode has features applied directly or directly on the carrier substrate which are a protective structure that can be transferred from a first, open state into a second, closed state which encloses the carrier substrate region which is wrapped into a tube, at least axially to the wrapping axis in parts and completely in the peripheral direction of the tube.

The basis of the protective structure configured in accordance with the invention relates to a wrapping or sheathing for the cuff electrode applied along a nerve fiber bundle for the purpose of mechanical protection and additional holding of the cuff electrode, in particular for the carrier substrate region which is wrapped to form a straight cylindrical tube that directly contacts the nerve fiber bundle. The protective structure is also able to form a barrier against cell at least one of and tissue growth overgrowing the cuff electrode.

To make handling as easy as possible for the doctor, the protective structure according to the invention is inseparably applied either directly on the carrier substrate of the cuff electrode or directly to an electrical supply and outlet structure, which is preferably connectable to the cuff electrode by a detachably fixed joint connection. In this way the doctor can apply the protective structure indirectly or directly attached to the carrier substrate immediately after applying the cuff electrode around the nerve bundle in a constructively precisely predetermined location and position in relation to the cuff electrode. Time-consuming positioning and centering of the protective structure relative to cuff electrode is no longer necessary due to the spatially firmly predetermined allocation between the protective structure and cuff electrode. It is also ensured that separation of the protective structure from the implant is prevented.

Preferably, the protective structure is directly or indirectly connected by a web-like connecting section to the carrier substrate. In the case of direct application of the protective structure to the carrier substrate, the preferred film protective structure is connected monolithically by a web connecting section to the carrier substrate.

The application, as well as the shape and size dimensioning of the at least one connecting section, is preferably selected so that the film protective structure assumes a distinct position and location relative to the carrier substrate section which is wrapped to form a tube so that the doctor can clearly and securely transfer the protective structure from the first, open state for the purpose of surrounding or sheathing, into the second, closed state, enclosing the first substrate section wrapped to form a tube. The protective structure preferably axially and in the peripheral direction completely covers the carrier substrate section wrapped to form a tube. Preferably the axial extent of the protective structure is larger than the cuff electrode, so that in the closed, second state, the protective structure axially projects beyond the second carrier substrate section of the cuff electrode wound to form a tube on both sides, with an overlap in each case. The cuff electrode becoming overgrown by surrounding tissue over the course of time is reliably prevented.

Depending on the design and form of the film carrier substrate of the cuff electrode, the protective structure can also be directly, preferably monolithically, connected to the carrier substrate, without the provision of a web connecting section.

In order to ensure that the protective structure, in the second, closed state, cannot become loosened from the cuff electrode in an uncontrolled manner, a preferred example of embodiment envisages a joining mechanism attached to the protective structure which, through forming at least one of a positive and non-positive connection, the protective structure is secured in the second, closed state. The joining mechanism is preferably a locking mechanism. Velcro-type connection structures and at least one of a strip or thread-like fastener can also be applied to the protective structure, which through the formation of at least one of loops and knots ensures durable, firm holding of the protective structure on the cuff electrode.

In a preferred embodiment, the protective structure has two cylindrical half shells, which, mutually are at least one of complementing and overlapping each other and enclose a straight cylindrical hollow space, in which the carrier substrate section is wrapped to form a tube and a nerve bundle, around which the cuff electrode is applied, to be seamlessly housed.

The two cylindrical half shells are preferably connected to each other in one piece, to monolithically, and preferably by way of a solid body joint to be transferable from an open state into a closed state, to enclose the cylindrical hollow space through a simple folding procedure. In the area of the directly adjoining or partially overlapping half shell edges, at least one joining mechanism of the previously described type is provided, which is preferably configured in the form of a locking mechanism. Alternatively to, or in combination with the locking mechanism, at least one strip or thread fixing is provided, which through suitable fastening openings applied within the half shells is fixable by way of at least one of loops and knots.

A further embodiment has a configuration of the protective structure as a film wrap-around cuff, which in each case comprises a single, flat, wrapping encompassing a cylindrical hollow space. Preferably, in this case the protective structure has a greater film thickness compared with the carrier substrate thickness of the first carrier substrate section of the cuff electrode wrapped in a tube. This is especially so since the protective structure should have as much material-inherent shape-retaining material stiffness as possible in order to be able to exert a protective retaining force on the cuff electrode inside it. In this case, an additional joining mechanism can hold the protective structure in the closed state as a mechanical lock.

In addition to at least one of the pure fastening and holding function as well as protection against tissue growth, a further preferred embodiment of the protective structure has an electrosensor function. Thus, on its surface radially facing away from the wrapping axis in its closed second state, the protective structure has at least one contact electrode which is connected to an electrical conducting structure integrated within the protective structure that extends along the second carrier substrate section. In this way, in the implanted state, the at least one contact electrode which is applied on the outer side of the protective structure comes into physical and electrical contact with the extravascular tissue environment, through which electrical signals can be picked up which can be utilised for diagnostic signal recording, for example as ECG signal tapping.

The electrodes within the cuff electrode, as well as the aforementioned at least one contact electrode attached to the surface of the protective structure are each contacted via electrical leads running within at least one of the carrier substrate of the cuff electrode and the protective structure, which all are coupled to the supply unit, preferably in the form of a control and electrical energy source unit, implanted separately to the cuff electrode.

The electrical supply and discharge structure extending between the cuff electrode and the implantable electrical supply unit, is preferably connected to the carrier substrate of the cuff electrode via an electromagnetic connecting structure, preferably in the form of a plug connection. By way of the at least one connecting section, the protective structure according to the invention is either connected directly in one piece to the second carrier substrate section of the cuff electrode or applied with the electrical supply and discharge structure to or as close as possible to the electromechanical connection.

Moreover, the carrier substrate of the cuff electrode and the film-like protective structure are connected to each other in one piece in a thin layer or a thin film and have the thickness of a thin layer or thin film in the range between 5 µm and 50 µm which is preferably between 5 µm and 20 µm.

BRIEF DESCRIPTION OF THE DRAWINGS

As an example, the invention will be described below, without restricting the scope of the invention, by way of examples of embodiment with reference to the drawings. Here.

DETAILED DESCRIPTION OF THE INVENTION

Figure 1A:
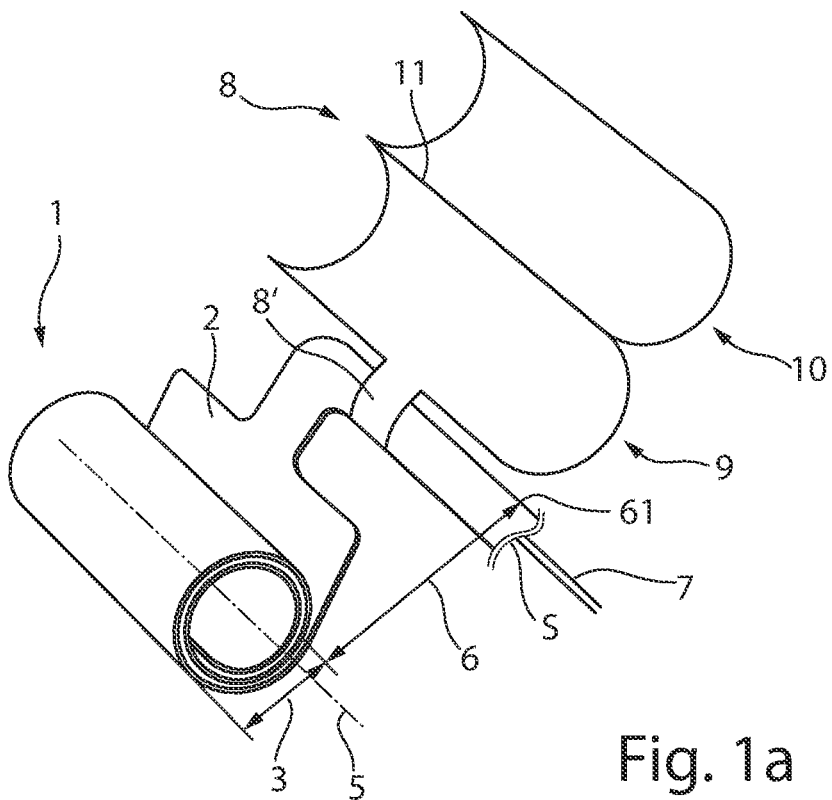
FIGS. 1a, b show cuff electrodes with a protective structure in the open state a) and in the closed state b)
Figure 2:
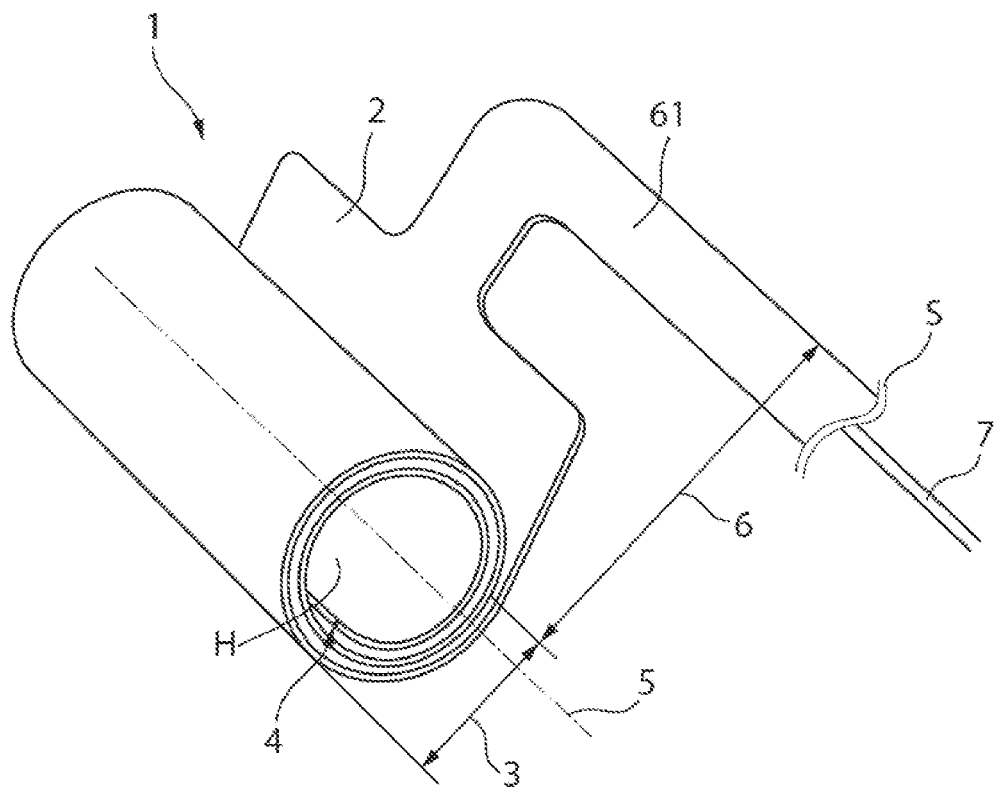
FIG. 2 shows cuff electrodes in accordance with the prior art.
Figure 3:
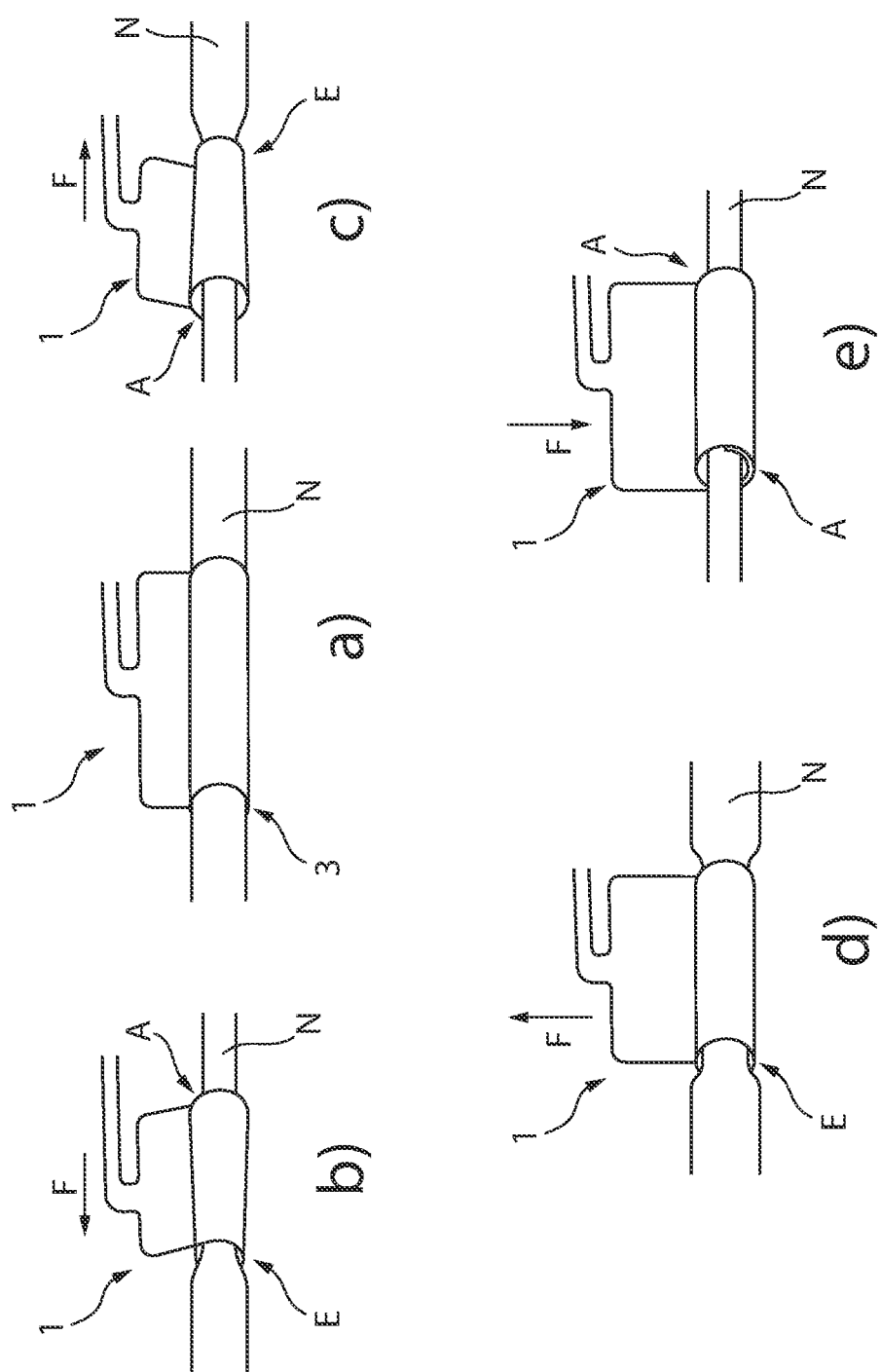
FIGS. 3a-e show different stress states of the cuff electrode on a nerve bundle.

FIG. 1a shows a medical implant 1 as a wrap-around cuff electrode or cuff electrode as already presented in FIG. 2, with the carrier substrate section 3 of the carrier substrate 2 formed by wrapping at least one and a half, and preferable two or multiple times about the wrapping axis, and through a material which inherently or a pre-determined material which is pre-tensioned to assume the shape of a tube in which the cuff electrode can be fixed in a self-supporting manner immovably on the peripheral edge of a nerve. Already discussed are the components of the medical implant 1 with reference numbers which will not be described again in order to avoid repetition.

In order to mechanically protect the carrier substrate region 3 of the cuff electrode wrapped around the wrapping axis 5 to form a tube, a protective structure 8 is provided, which via a weblike connecting section 8', is connected to the carrier substrate 2 at the second carrier substrate region 6 and more particularly on the weblike surface section 61. The protective structure 8 as well as the web connecting section 8' are made of the same film material as the carrier substrate 2 of the cuff electrode which is preferably a thin film or a thin layer of polyamide film, which preferably has a film thickness in the range between 5 µm and 20 µm. The connecting section 8' and the carrier substrate 2 are preferably monolithically connected.

The protective structure 8 comprises two cylindrical half shells 9, 10 which are monolithically connected to each other, preferably by way of a solid body joint 11. The solid body joint 11 is preferably a crease.

Figure 1B:
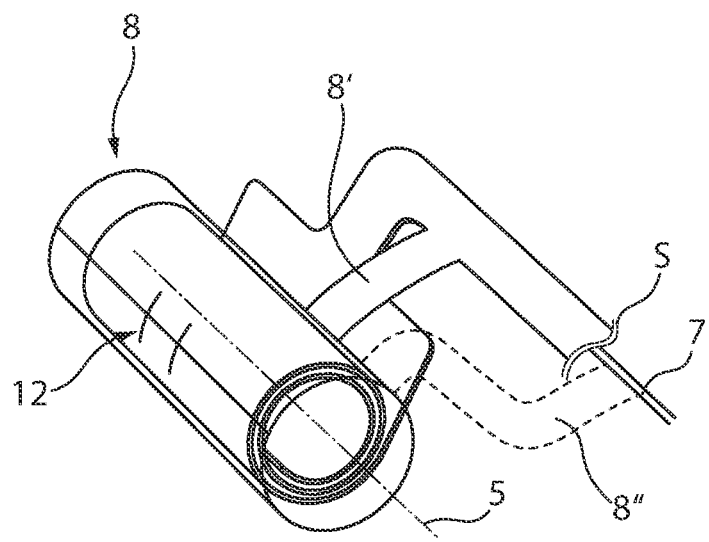

After applying the medical implant 1 along a nerve fiber bundle, for the purpose of mechanically protection, the protective structure 8 shown in the open state according to FIG. 1a is transferred into the closed state according to FIG. 1b, through which both half shells 9, 10 are joined, forming a straight hollow cylinder around the first carrier substrate region 3 wrapped in a tube. The closed state of the protective structure 8 shown in FIG. 1b, in which for better illustration both half-shells 9, 10 are each shown transparently, indicates that the hollow cylindrically-shaped in a closed protective structure 8 that completely encloses the wrap-around cuff contained therein both in the peripheral direction and also axially to the wrap axis 5. In the closed state, the protective structure 8 preferably has an axial excess portion on each side facing the wrap-around cuff, so that that the internally arranged wrap-around cuff is prevented from being functionally impaired by tissue growth.

Both half shells 9, 10 of the protective structure 8 are joined together as a complete straight hollow cylinder, which can advantageously be held permanently in the closed state by a joining mechanism 12 which is only shown schematically.

As an alternative to applying the web connection section 8' directly to the surface section 61, it is also possible, to connect the web-like connecting structure 8" indicated with the dashed line in FIG. 1b, so that the connecting structure 8" leads away from the implant 1, preferably in the immediate vicinity of the interface S.

Figure 4A:
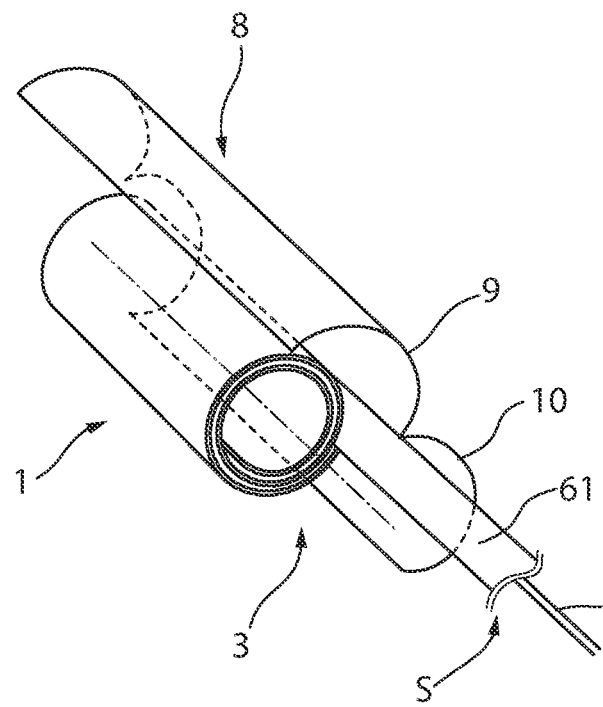
FIGS. 4a, b show an alternative design of the cuff electrode and application of the protective structure.
Figure 4B:
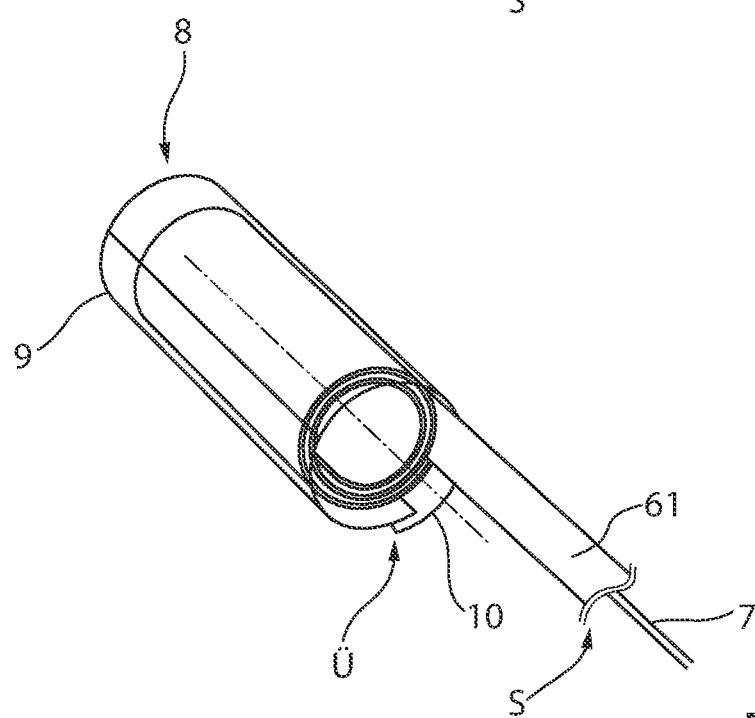

FIGS. 4a and b show an alternative embodiment of the medical implant as the cuff electrode 1 which largely comprises a carrier substrate region 3 wrapped to form a tube, from which a surface section of the carrier substrate leads off directly, along which the electrical leads 7, (not shown in detail,) lead off. The protective structure 8, which like the embodiment in FIGS. 1a, b comprises two half shells 9, 10, which directly adjoins the carrier substrate region 3 without any connecting structure. In FIG. 4b, the closed state of the protective structure 8 is illustrated. To facilitate better understanding, the protective structure 8 is shown transparently. In this form of embodiment, the end edges of the half shells 9, 10 overlap along an overlap Ü.

Figure 5A:
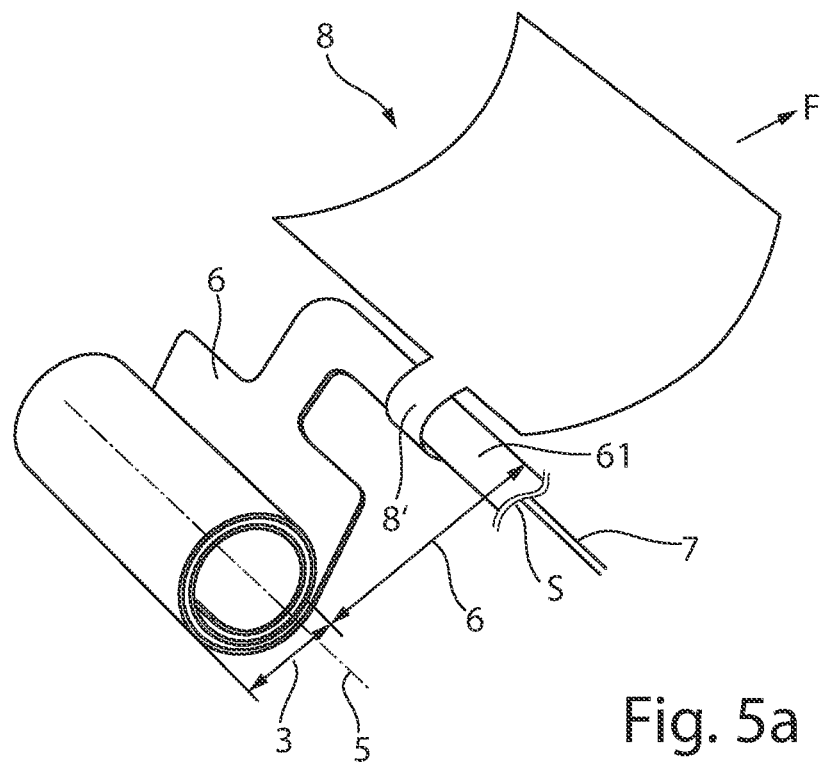
FIGS. 5a, b show an alternative design of a protective structure in the open state a) and in the closed state b)

In FIG. 5a, an alternative design of the protective structure 8 is shown. In this case, the protective structure 8 is a film-like surface section into which are material inherently or mechanically pre-tensioned is introduced so that the protective structure 8 can only be held in the open state as shown in FIG. 5a when an external force F is applied. Like the protective structure 8 illustrated in FIG. 1a, the flatly configured protective structure 8 is monolithically connected to the second carrier substrate region 6, particularly at the surface section 61 by way of a weblike connecting section 8'.

Figure 5B:
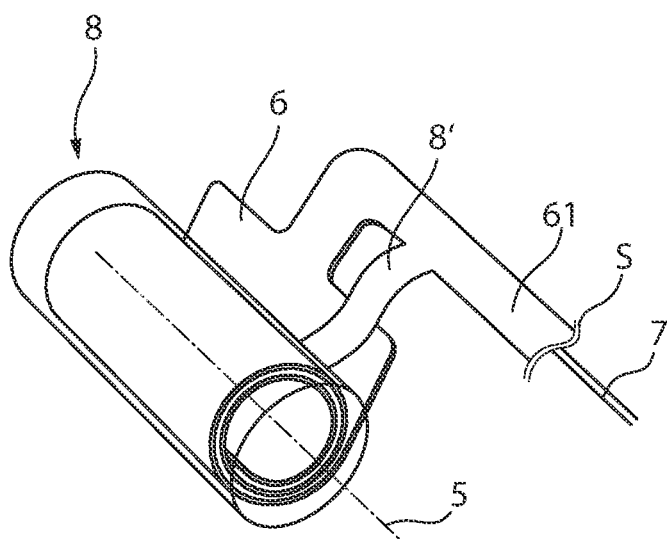

After application of the cuff electrode to the nerve bundle, the protective structure 8 is transferred into the closed state according to FIG. 5*b*, wherein the surface section of the protective structure 8 reshapes itself as a result of the inherent mechanical pre-tensioning to form a straight hollow cylinder. The holding force, through which the protective structure 8 is kept in the closed state, can preferably be increased in that the thickness of the surface section of the protective structure 8 is selected to be correspondingly greater, for example larger than the film thickness in the area of the carrier substrate 2.

As has already been mentioned, measures regarding the an additional joining mechanism as well as an alternative application of the protective structure 8 with the connecting structure 8' without the connecting structure, that is by direct application of the protective structure 8 to the carrier substrate region 3, is comparable with the embodiment of the cuff electrode in accordance with FIGS. 4*a, b*, which can be used in the case of the example of embodiment shown in FIG. 5 and b.

Figure 6:
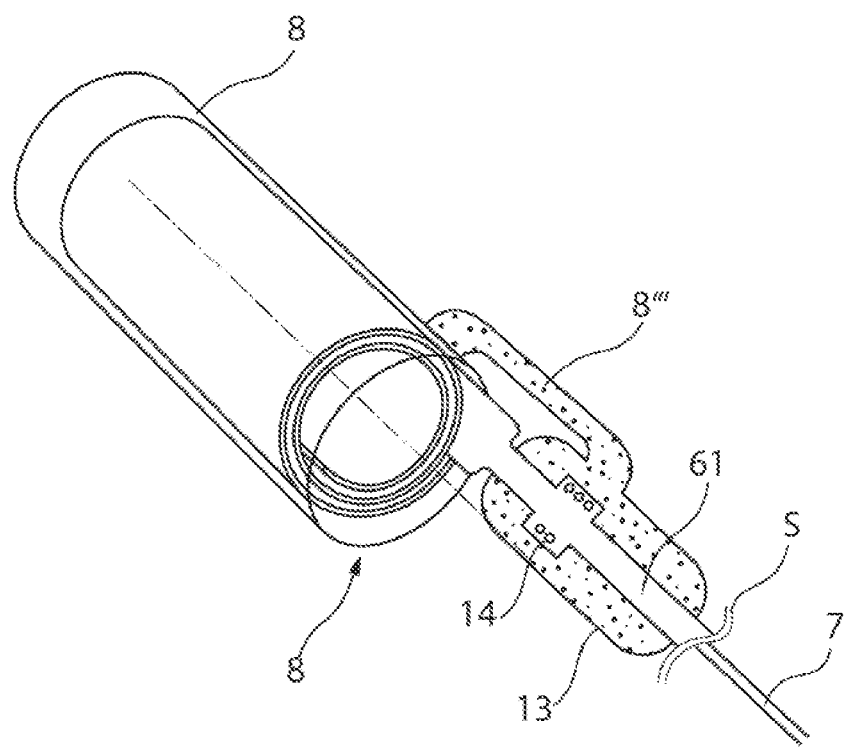
FIG. 6 shows an alternative design and application of the protective structure.

FIG. 6 shows a protective structure 8 in the closed state, which 8 encloses the cuff electrode situated within it. Protective structure 8 can be two half shells, as shown in FIGS. 1*a, b*, or as a wrap-around cuff as shown in FIGS. 5*a, b*. In contrast to the illustrated forms of embodiment, in this case the protective structure 8 is connected via a connecting structure 8" with a sheathing 13 made of elastomer material, preferably of silicone or a silicone-based plastic, which surrounds at least one section of the surface section 61. The preferably tubular sheathing 8 is joined in a positive manner to the film-like surface section 61 by way of an anchoring structure 14 applied in one piece to the surface section 61. The surface section 61 is part of the carrier substrate 2 and directly or indirectly adjoins the carrier substrate region 3 of the cuff electrode wound to form a tube. The shape and size of the sheathing 13 are selected for the purpose of intracorporeal application to a nerve fiber bundle, is made easier for a doctor to handle. Not necessarily, but advantageously, the protective structure 8 is made of the same material from which the sheathing 13 is made.

LIST OF REFERENCE NUMBERS

1 Medical implant
2 Carrier substrate
3 First carrier substrate region
4 Free section end
5 Wrapping axis
6 Second carrier substrate region
61 Weblike surface section
7 Connecting structure
8 Protective structure
8', 8", 8''' Connecting section
9, 10 Half shells
11 Solid body joint
12 Joining mechanism
13 Sheathing
14 Anchoring structure
Ü Overlap

The invention claimed is:

1. A wrap-around cuff electrode configured as a medical implant into a patient comprising:
  a flexible biocompatible film substrate including a substrate region comprising more than one wrap-around layer of the flexible biocompatible film substrate with ends which are loose to flex in response to movement of a person when the cuff electrode is implanted and forms a tube for containment of a nerve bundle of the patient; and
  a protective tube with the ends applied to the flexible biocompatible film substrate including an axial excess portion on each end facing the cuff electrode which is configurable from a first open state to a second closed state axially enclosing at least part of the substrate region and completely enclosing the tube in a peripheral direction of the tube, and the axial excess portion on each end of the cuff electrode including means for preventing growth of tissue axially into the tube.

2. The medical implant according to claim 1 wherein the protective structure when closed in the second closed state completely covers the substrate.

3. The medical implant in accordance with claim 2 wherein the protective structure in the second closed state has a surface facing radially away from a wrapping axis to which at least one contact electrode is connected with an electrical conducting structure integrated within the protective structure and extending along the substrate.

4. The medical implant in accordance with claim 3 wherein:
  the substrate region is one piece wrapped into the tube which includes a second substrate region on which an electromechanical connection, an electrical supply and a discharge is attached and the protective structure is attached to the electrical supply and discharge.

5. The medical implant in accordance with claim 4 wherein the second substrate region is surrounded at least in part by a sheath of elastic material.

6. The medical implant in accordance with claim 5 wherein the protective structure is connected in one piece to the sheath.

7. The medical implant according to claim 1 comprising a joining mechanism on the protective structure which is detachable and secures the protective structure when in the second closed state.

8. The medical implant according to claim 1 comprising:
  the protective structure is connected by at least one web to the substrate.

9. The medical implant in accordance with claim 1 wherein the protective structure comprises two half shells which are mutually complimentary to each other when the protective structure is in the second closed state to enclose a cylindrical hollow space.

10. The medical implant in accordance with claim 1 wherein the protective structure is a wrap around film cuff comprising a flat wrap which is wrapped to enclose a cylindrical hollow space.

11. The medical implant in accordance with claim 1 wherein a predetermined material is located in the first substrate region which, without any external force, is shaped into a wrapping configuration in which an end of the substrate region is radially covered by at least one wrapped layer of the substrate.

12. The medical implant in accordance with claim 1 wherein the substrate and the protective structure are each a layer of film and have a thickness from 5 micrometers to 50 micrometers.

13. The medical implant in accordance with claim 1 wherein the substrate is a flexible biocompatible substrate shaped into a tube by wrapping around an axis.

* * * * *